US012806306B2

(12) United States Patent
Lang

(10) Patent No.: US 12,806,306 B2
(45) **Date of Patent: *Nov. 24, 2026**

(54) SINGLE USE, TOPICAL, HYDROPHILIC ARTICLE WITH AN ACCESSIBLE HEMOSTATIC FOAM

(71) Applicant: David Lang, Vonore, TN (US)

(72) Inventor: David Lang, Vonore, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/299,304

(22) Filed: Aug. 13, 2025

(65) Prior Publication Data

US 2025/0367339 A1 Dec. 4, 2025

Related U.S. Application Data

(63) Continuation-in-part of application No. 18/634,841, filed on Apr. 12, 2024, now Pat. No. 12,447,227, (Continued)

(51) Int. Cl.
*A61F 13/00* (2024.01)
*A61L 15/26* (2006.01)
(Continued)

(52) U.S. Cl.
CPC ............ *A61L 15/425* (2013.01); *A61L 15/26* (2013.01); *A61L 15/28* (2013.01); *A61L 15/58* (2013.01); *A61L 2400/04* (2013.01)

(58) Field of Classification Search
USPC .................................................... 604/180
See application file for complete search history.

(56) References Cited

U.S. PATENT DOCUMENTS 4,373,519 A 2/1983 Errede
5,792,089 A * 8/1998 Penrose ............. A61F 13/0203 602/57
(Continued)

FOREIGN PATENT DOCUMENTS

WO WO-2020154175 A1 7/2020
WO WO-2021263030 A1 * 12/2021 ......... A61F 13/0269

OTHER PUBLICATIONS

Johnson & Johnson, Ethicon, Biopatch(R) Protective Disk with CHG, Product disclosure jnjmedtech.com/en-US/news-events/united-under-the-johnsons-and-johnson-name.
(Continued)

*Primary Examiner* — Kim M Lewis
(74) *Attorney, Agent, or Firm* — MARK A. LITMAN & ASSOCIATES, P.A.

(57) ABSTRACT

A hemostatic surface application device has a region of hemostatic foam for contact with a patient's skin about a wound. The device includes: a release layer, the release layer is in contact with a hemostatic flexible foam layer, a structural foam layer surrounds the hemostatic flexible foam layer, forming a central hemostatic surface exposed through s front side of the surrounding structural foam layer, and a support layer is adhered to the back side of the structural foam layer;

wherein the support layer has an opening therein exposing at least 5% of the back side of the structural foam layer to enable water to irrigate the structural foam layer during removal of the device from contact with a patient's skin, and there is a slit through a), b) and c) which allows insertion of a liquid-feeder tube enabling liquid flow to and from the hemostatic flexible foam layer.

20 Claims, 6 Drawing Sheets

Related U.S. Application Data which is a continuation-in-part of application No. 17/168,128, filed on Feb. 4, 2021, now Pat. No. 11,975,114.

(51) Int. Cl.

| | |
|---|---|
| ***A61L 15/28*** | (2006.01) |
| ***A61L 15/42*** | (2006.01) |
| ***A61L 15/58*** | (2006.01) |

(56) References Cited

U.S. PATENT DOCUMENTS

| | | | | |
|---|---|---|---|---|
| 6,060,461 | A | 5/2000 | Drake | |
| 6,150,505 | A | 11/2000 | Marx | |
| 6,992,233 | B2 | 1/2006 | Drake et al. | |
| 11,975,114 | B2 * | 5/2024 | Lang | A61L 15/24 |
| 12,420,007 | B2 | 9/2025 | Rice et al. | |
| 12,447,227 | B2 * | 10/2025 | Lang | A61L 15/28 |

OTHER PUBLICATIONS

StatSeal(R) Powder—Faster & Safer Hemostasis Biolife News Published Product Disclosure.

* cited by examiner

SINGLE USE, TOPICAL, HYDROPHILIC ARTICLE WITH AN ACCESSIBLE HEMOSTATIC FOAM

RELATED APPLICATION DATA

This application is filed under 35 U.S.C. 120 and claims priority as a Continuation-in-Part from U.S. patent application Ser. No. 18/634,841, filed 12 Apr. 2024, now U.S. Pat. No. 12,47,227; which in turn claims priority as a Continuation-in-Part from U.S. patent application Ser. No. 17/168,128, filed 4 Feb. 2021, now U.S. Pat. No. 12,311,063. Thes applications are incorporated by reference in their entireties herein by reference.

BACKGROUND OF THE INVENTION

1. Field of the Invention

The present invention relates to the field of topical, substantively non-transferring application of a medicinal or therapeutic device to tissue particularly for the reduction of bleeding, especially for enhancing the formation of clots on the surface of patients as wound dressing applied over vascular puncture sites and percutaneous catheter sites.

2. Background of the Art

External wounds and concomitant bleeding are the most common injuries suffered by animals. Scratches, cuts, abrasions, lacerations, punctures and other categories of damage to layers of tissue, especially skin, each act to breach the protective tissue and blood vessels, allowing blood to flow out of its normal passageways. Bleeding provides a first line defense against damage from the ancillary effects of the trauma that caused the injury. The flow of blood washes material out of the wound and the blood clots to seal the wound area. The types of materials washed from the wound by the flow of blood from the traumatized area includes material introduced into the wound area by any foreign object which caused the wound (including biological species such as bacteria and viruses and inorganic species such as particulates). The clotting prevents migration of materials into the wound area, and therefore into the animals' body, thus reducing the likelihood of subsequent infection of the wound, even after materials originally introduced into the wound have been removed or reduced in volume by the initial blood flow.

Clotting is essential to both the short term and long term process of healing the wound. In the short term, after the wound has been partially cleansed by blood flow, the clotting entraps these removed materials so that they will not easily reenter the wound and stops the blood flow so that excessive blood loss will not occur. In the long term, the clot secures the wound minimizing additional tissue trauma (e.g., from flexing of the area) and preventing additional contaminants from entering the wound and blood stream.

Clotting is a complex biological process, driven by a series of cascading organic/biological chemical reactions which must occur in a specific sequence to cause the final effect of protecting the wound. In lay terms, the events in a simple wound where blood flow has occurred can be described as following a reaction path where a) Blood cells leak into a wound area; b) Blood vessels usually contract in the wound area to reduce the flow of blood; c) Platelets in the blood aggregate and adhere to tissue at the damaged site, even plugging small blood vessels; d) Platelets also interact with collagen, phospholipids, and tissue factor (a lipid-containing protein or lipoprotein, that stimulates blood clot formation); e) The platelets break-up and release thromboplastin, a poorly defined mixture of phospholipids and proteins that activate a series or cascade of reactions, usually catalyzed by serine proteases. The final product of these reactions is the enzyme thrombin which catalysis the conversion of the soluble blood protein, fibrinogen, to insoluble fibrin; f) The platelets provide nuclei upon which fibrin is bound to form the first stage of the moist clot, followed by subsequent maturation of the clot to form a firm coherent mass; g) Tissue forming cells, fibroblasts, approach the wound and associate with the moist clot to strengthen the region; h) The clot contracts and dehydrates, usually through evaporative processes, although there may be some absorption of liquid into the tissue; i) Phagocytes (white blood cells) move into the wound area to ingest microorganisms, cellular debris and any residual foreign matter; j) Epidermal cells at the edge of the wound divide and build a bridge across the wound.

The actual chemical and biological processes involved in the clotting process are quite complex and sophisticated. The process must be very selective, forming clots under only exacting conditions, so that clot formation does not occur in the circulatory system where clotting would itself be dangerous, causing phlebitis and certain types of strokes.

Wound management and clotting enhancement for wounds has taken many different paths over the years. There are a wide variety of different methodologies available for the management of wounds, depending, at least in part upon the type of wound and its severity. The two most common and effective treatments for minor bleeding wound management, following cleansing of the wound area, include direct application of pressure to the wound area and the topical application of an absorptive bandage to the wound surface. To assure the reduction of direct or secondary infections, all wound management should include cleansing and application of an antimicrobial agent to the wound area. After this cleansing step, the other methods may follow to control bleeding and prevent contamination of the wound. Direct application of pressure is usually effected by application of pressure manually or with a light wrapping. A sterile article is placed over the wound and pressure applied to the wound through the sterile article (e.g., a fabric, such as gauze, cotton ball, bandage, or other available, preferably sterilized or at least cleaned fabric). The pressure acts to assist in closing blood vessels in the area to reduce blood flow, absorb some of the initial blood flow with the highest content of foreign matter carried therein, and to stabilize the movement of the blood so that clotting is given time to initiate. The application of bandages to the wound area primarily acts to absorb excess blood, flow, provide a longer term barrier over the wound against introduction of foreign agents, protect the clot while it is still fragile (allowing it to dehydrate in the first twenty-four hours), and possibly carry and retain antimicrobial material to the wound surface.

The use of lasers, alone or in combination with topically applied patch materials (e.g., an elastin patch made from animal tissue), has been suggested for field treatment of bleeding wounds, both internal wounds and external or topical wounds. This has been specifically suggested as a field treatment, especially for the military, police, fire, and rescue services. Lasers by themselves can cauterize and seal vessel and organ wounds, and the patch can provide additional structural support for the area. http://detnews.com/96/discover/9701/05/12300058.htm.

Many folk remedies have also been applied as abrasion, but not open wound, treatments. For example, www://.drchristopher.com/ail/abrasio3.htm suggests the use of specific natural material treatments for abrasions where the skin has not been broken. The natural herbal agents include wheat grass chlorophyll, comfrey, healing ointment (comfrey, marshmallow, marigold, beeswax and oils), myrrh, plantain (and banana is also well known), and cayenne pepper. These materials may be applied directly to the abrasion area or carried on another surface, often with wetting suggested to retain the herbal abrasion treatment material. An Asian home remedy includes Dit Da Jao ("Iron Wine) which is a tincture remedy applied to relieve pain, stimulate blood flow and chi flow, and break up clots and bruises. The tincture is made up from powdered herbs and alcohol, with strained herbal residue discarded and the liquid tincture applied to the wound surface. The herbs to be used include *Arnica* blossom, comfrey, blessed thistle, goldenseal root, ginger root, Myrrh, *sarsaparilla* root, and witch hazel. Http://www.aikidofaq.com/n.sub.--section51.html)

Newer technology for wound management is the use of chemical bandages, or literally polymeric film-forming material over the wound area. This technology has passed from a fairly unsophisticated application of liquid glues (e.g., cyanoacrylate adhesives, gelatinous glues, and UV curable polymers) to the wound surface. In 1998, only the second liquid glue was granted FDA approval for use as stitches in addition to clotting enhancement, the glue apparently comprising a formaldehyde content cyanoacrylate. This glue is Closure Medical Corporation's DermaBond™, which is used as an alternative to Baxter HealthCare Corporation's Tisseel™, which is made from two blood proteins that naturally cause blood to clot. The cyanoacrylate must have a strong tendency for tissue irritation and carries a standard recommendation against use with patients with sensitivities to acrylates and formaldehyde, which are fairly common. Baxter HealthCare Corporation's Tisseel™, which is made from specific blood proteins thrombin and fibrinogen, is relatively expensive to manufacture. In addition, the use of human or animal derived protein compositions carries the risk of contamination by infectious agents such as hepatitis viruses, Human Immuno-Deficiency (HIV) viruses, or prions such as have been related to mad cow disease (bovine spongiform encephalitis) and Creutzfeld-Jakob disease. The Cryoseal™ clotting system uses cryoprecititated proteins obtained from the patients' blood as an adhesive. This fibrin glue adhesive is prepared and applied using a floor-standing, air-driven device in an operating theater.

U.S. Pat. No. 6,060,461 describes a method for enhancing the formation of clots on a wound of an animal where blood is present comprising the steps of applying porous particles with dimensions of from about 0.5 to 1000 micrometers to at least a portion of said wound where blood is present in said wound, allowing said porous particles to remain in contact with said blood in said wound while clotting initiates in said wound. The porous particles may have molecular sieve cutoff values between about 5,000 Daltons and 200,000 Daltons. The pores may comprise from 5 to 75% by volume of the porous particles.

PCT Application Publication WO 00/27327 describes a novel hemostatic composition comprising a substance containing uncharged organic hydroxyl groups and a substance containing at least one of a halogen atom and an epoxy group, which composition induces rapid blood coagulation and hemostasis at a wound or bleeding site. Examples of methods of application of the composition include, but are not limited to bags of materials, patches and bandaid-type patches, segments to be packed into cavities, fibers, fabrics, and the like.

It is known that fibrin clots are formed in vivo based upon the reaction of fibrinogen and thrombin in the presence of calcium ions. The initial phase of wound healing starts after the formation of fibrin clot, and involves the mobilization of cells from surrounding undamaged tissue. Normally, the earliest cells mobilized to the wound are inflammatory where they are active for a period of at least 1-3 days following injury. Subsequently, they are displaced by cells of the mesenchyme lineage which are immobilized into, navigate through and digest fibrin and replace fibrin with extracellular matrix (ECM) of different collagen types, fibronectin and hyaluronan. Endothelial cells also infiltrate the fibrin and generate microcapillary structures. Ultimately, these cells replace the provisional fibrin matrix with granulation tissue populated by parenchymal cells and vasculature in secreted ECM.

Human fibroblasts are the major cellular entities responsible for the regeneration of the extracellular matrix (ECM) within the wound bed. Human fibroblasts also express specific membrane receptors to fibrinogen and thrombin. In the case of skin wounds, human fibroblasts reform the matrix of the dermis. For example, during the course of healing of an incisional skin wound, human fibroblasts are mobilized from the surrounding tissue and enter into the fibrin clot, help dissolve it and generate as well as reform the collagens (i.e. type I and type III) in the extracellular matrix. Based upon these properties of human fibroblasts, fibroblast implants have been suggested as a means for supplementing the body's natural wound healing regime (Gorodetsky, R., et al. Radiat. Res. 125:181-186 (1991)).

Benzoylated hyaluronic acid (HA) sheets containing holes or pores have been used as a carrier for fibroblasts and keratinocytes for wound healing (Andreassi, L., et al. Wounds 3(3): 116-126 (1991)). Specifically, HA sheets are cultured with these cells and then affixed to the site of the burn injury, where the cells migrate out of the sheet and accelerate the rate of wound regranulation. A major problem with implanted HA sheets, however, is that they are not metabolized by tissue, are cumbersome to administer, and may result in long-term immunological problems.

Purified fibrin(ogen) (which is known in the art as a mixture of fibrin and fibrinogen) and several of its lytic fragments (i.e. FPA, FPB, D and E) have been shown to be chemotactic to a variety of cells including macrophages, human fibroblasts (HF) and endothelial cells (Gorodetsky, R., et al. J. Lab. Clin. Med., in press (1997); Brown, L. F., et al. Amer. J. Pathol. 142:273-283 (1993); Clark, R. A. F., et al. J. Invest. Dermatol. 79:624-629 (1982); Ciano, P. S., et al. Lab. Invest. 54:62-69 (1986); Dejana, E., et al. J. Clin. Invest. 75:11-18 (1985)). Thrombin also has been shown to exert proliferative effect on various cells including fibroblasts, endothelial cells, and to enhance wound healing in rat skin (Kang, Y. H., et al. J. Histochem. Cytochem. 39:413-423 (1991); Shuman, F., NY Acad. Sci. 408:228-235 (1986); Biedermann, B., et al. J. Lab. Clin. Med. 124:339-347 (1994)).

Fibrin microbeads have been described in the prior art for use as drug delivery systems ((Ho, et al. Drug Dev. and Ind. Pharm. 20(4):535-546 (1994); Senderoff, et al. J. Parenteral Sci. & Tech. 45(1):2-6 (1991)). However, it has not been suggested or taught in the prior art that such fibrin microbeads have chemotactic and/or proliferative effects on any cells. Furthermore, the fibrin microbeads of Ho, et al. and Senderoff, et al. would not be particularly useful or desirable as vehicles for culturing cells. In this regard, the Ho, et al. microbeads contain glutaraldehyde which cross-links proteins and destroys certain biologically active sites, thereby interfering with the binding of the microbeads to cells. Glutaraldehyde treatment may also render the microbeads immunogenic. The Senderoff, et al. microbeads contain essentially the same relatively low degree of cross-linking as fibrin. Thus, the Senderoff, et al. microbeads are not stable in aqueous solutions and therefore would not be useful as vehicles for culturing cells which require matrices that do not readily dissolve in aqueous solutions. U.S. Pat. No. 6,150,505 describes novel fibrin microbeads and their method of manufacture, where the fibrin microbeads are provided in the absence of glutaraldehyde.

One problem in the use of these medical or medicinal treatments is the application of the solids, particulates, fluid or otherwise flowable materials to the desired site. Sprinkling a material over the surface of a wound is effective, but can waste significant amounts of materials. It is desirable to be able to apply the materials more uniformly and specifically to a site. U.S. Pat. No. 6,241,697 shows a non-contact wound covering for covering a wound. A peripheral sealing ring is covered by a barrier layer and this assembly is attached to the skin with an adhesive. The barrier layer and peripheral sealing ring together define a treatment volume over the wound. The barrier layer may include active and passive heaters and the sealing ring may dispense water to control the humidity of the treatment volume. One form of active heat is the transfer of a heated fluid to the wound covering. In effect, an enclosed area is defined around a wound and liquid is directed into the enclosed area through a hose or tube.

U.S. Pat. No. 4,373,519 provides a system for removing liquids from a wound to promote healing, and embeds absorbent materials into a non-woven web that is applied to a surface. The non-woven web may be adhesively secured to the wound area.

U.S. Pat. No. 6,992,233 (Drake) describes a hemostatic starch delivery system including a delivery system for the delivery of flowable medicinal, therapeutic or medicine materials has a strip with flowable material contained and restrained therein. A removable seal is provided, so that when the removable seal is removed, the flowable material will flow from a storage area onto a site selected for treatment. The removable seal may be provided with additional features such as absorbent coatings, or additional disinfectants coatings useful in preparing the wound surface to receive the flowable wound treatment material. A preferred composition is a system, article and method for the enhancement of clotting in wounds with extravascular blood flow, especially where the surface of the tissue has been broken.

Clot formation can be needed in many different environments and individual structures and improved or optimized compositions can be needed for each particular field of use.

SUMMARY OF THE INVENTION

A hemostatic surface application device having a region of hemostatic foam for contact with a patient's skin where a wound exists or is created, the device includes: a release layer, the release layer in contact with a hemostatic flexible foam section, and a structural foam layer having a front side and a back side surrounding the hemostatic flexible foam layer, forming a generally central hemostatic surface exposed through the front side of the surrounding structural foam layer, and a support layer adhered to the backside of the structural foam layer. The device has a through its depth slit that enables a hydration or medicine feeding tube to penetrate from an outside surface of the device into and or through the hemostatic flexible foam layer.

A topical (and topically-applied), substantively non-transferring application of a medicinal or therapeutic device to surface tissue is used particularly for the reduction of bleeding, especially for enhancing the formation of clots on the surface of patients as wound dressing applied over vascular puncture sites and percutaneous catheter sites. The device includes a non-dissolvable hemostatic foam carried on a support. A strippable/removable cover protects the foam until immediately before application and before insertion of a puncture or catheter through the applied device.

BRIEF DESCRIPTION OF THE FIGURES

FIG. 3 is a non-limiting rendition of chemical structure for a hemostatic foam useful un the practice of the present invention.

DETAILED DESCRIPTION OF THE INVENTION

Figure 1:
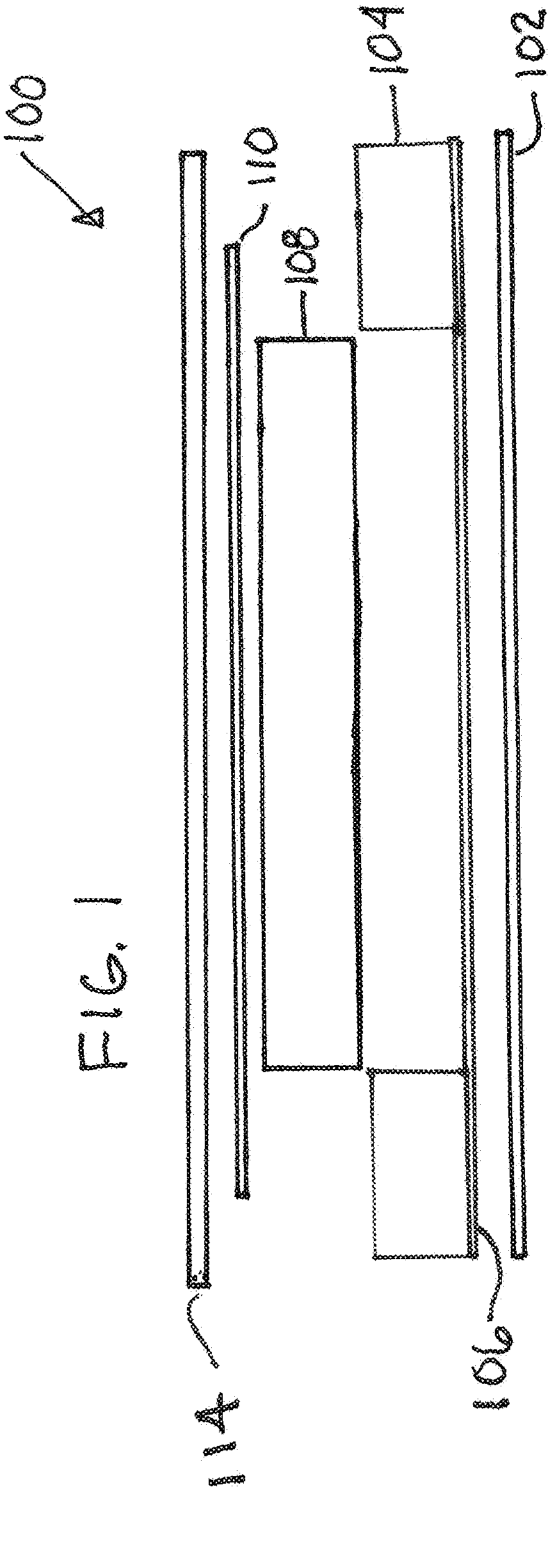
FIG. 1 is an exploded side view of an embodiment of the therapeutic device of the invention.

A hemostatic surface application device having a region of hemostatic foam for contact with a patient's skin where a wound exists or is created, the device including: a release layer, the release layer in contact with a hemostatic flexible foam section, and a structural foam layer having a front side and a back side surrounding the hemostatic flexible foam layer, forming a generally central hemostatic surface exposed through the front side of the surrounding structural foam layer, and a support layer adhered to the backside of the structural foam layer.

A blood-flow reducing, hemostatic surface application device, which resists or eliminates transfer of clotting material into a wound, is described as having a region of hemostatic foam for contact with a patient's skin where a wound exists or is created. The device may include a release layer. The release layer is in contact with a hemostatic flexible foam section, and a structural foam layer having a front side and a back side surrounding the hemostatic flexible foam layer. The surrounding structure of the structural foam forms a generally central hemostatic surface (of the hemostatic foam) exposed through the front side of the surrounding structural foam layer. It is desirable that a support layer is adhered to the back side of the structural foam layer. The hemostatic flexible foam layer should be able to retain at least 99.5% of total weight of the hemostatic flexible foam layer when in contact with a surface having a 5 micron thick layer of water on its surface for 1 minute. The hemostatic flexible foam layer may include a polysaccharide foam composition. The device may have the hemostatic flexible foam layer with a thickness at least 1% greater than the thickness of the structural foam layer. The structural foam layer may a polyurethane foam, either closed cell, open-cell or the like. Other foams may be used (as the foam has no chemical requirements except to be non-irritating to skin, and performs only a structural effect), such as polysiloxane foams, polycellulosic foams, and other polymeric foams. The device may have the support layer adhered to the backside of the structural foam layer by an adhesive layer.

A method of reducing excessive blood flow off an exterior surface wound of a patient comprising removing the release layer of the hemostatic surface application device as described above, and applying the generally central hemostatic foam layer to a limited area of skin of the patient. The method may be executed wherein, after applying the generally central hemostatic foam layer to a limited area of skin of the patient, a catheter or needle is inserted through the hemostatic foam layer of the hemostatic surface application device and into the skin of the patient. In this process, after inserting the catheter or needle through the skin of the patient, blood exudes from the skin of the patient and is clotted by the hemostatic foam layer. Furthermore in this method, the hemostatic flexible foam layer retains at least 99.5% of total weight of the hemostatic flexible foam layer when in contact with blood exuding from the skin of the patient for 1 minute.

Hemostatic foam compositions are known in the medical field, but they have had limited numbers of variations in structural forms within the field. Among known foams that can be used within the practice of the present invention are those shown by the following background art.

US Published Patent Application Document 2015/0314037 and 2014/0161738 (Andreas) discloses a pharmaceutical hemostatic liquid foam base preparation comprising albumin as foaming agent and a fibrinogen precipitating substance and optionally a coagulation inducing agent, wherein albumin as foaming agent is present in native form; a method for the production of a transient hemostatic liquid foam; the transient hemostatic liquid foam; and a kit for making the foam.

US Published Patent Application Documents 20170136054 and 20140010887 and 2009/0062233 (Ji) evidence a modified starch material for biocompatible hemostasis, biocompatible adhesion prevention, tissue healing promotion, absorbable surgical wound sealing and tissue bonding, when applied as a biocompatible modified starch to the tissue of animals. The modified starch material, which may be in the form of a foam, produces hemostasis, reduces bleeding of the wound, extravasation of blood and tissue exudation, preserves the wound surface or the wound in relative wetness or dryness, inhibits the growth of bacteria and inflammatory response, minimizes tissue inflammation, and relieves patient pain. The hemostatic materials, which may be in foam form, can be provided by adding the functional group on the raw starch glucose units with chemical agents, e.g. by carboxylation modification, or hydroxylation modification, the starch captures hydrophilic groups in its molecular structure and obtains hydrophilic properties, By using bifunctional or polyfunctional chemical agents to cross-link the raw starch macromolecules or grafting external macromolecular hydrophilic groups to the raw starch, the starch acquires enhanced hydrophilic properties and viscosity/adhesiveness in a water solution. The viscosity of modified starch relates to the raw starch origin and the degree of substitution of external and cross-linked or grafted functional groups, etc. When contacting blood, the hydrophilic and adhesive properties of the modified starch of the present invention produce a "starch-blood coagulation matrix" with strong adhesive characteristics which can seal wounded tissue and stop bleeding. In addition, the interaction between the formed blood coagulation matrix and the functional groups of tissue proteins causes the "starch-blood coagulation matrix" to adhere to and seal the wounded tissue, resulting in hemostasis.

US Published Patent Application Document 2013/0096479 discloses a hemostatic product having a plurality of hemostatic layers. Each of the hemostatic layers includes a dextran support and at least one hemostatic agent, which is selected from the group consisting of thrombin and fibrinogen. The hemostatic layers are arranged in a stacked configuration. The thrombogenic agent may be applied onto open-cell or closed-cell foam supports.

US Published Patent Application Document 2012/0114592 (Zuidema) is directed to hemostatic foams and to the preparation of such foams. In a first aspect, the present invention provides a biodegradable hemostatic foam comprising a polymer blend of a water-soluble polymer and a phase-separated polyurethane comprising an amorphous segment and a crystalline segment, wherein at least said amorphous segment comprises a hydrophilic segment.

US Published Patent Application Document 2007/0172432 (Stopek) discloses biodegradable hemostatic compositions, including nucleic acids. The nucleic acids may be obtained from plant sources, animal sources, or combinations thereof, or they may be synthetic. The hemostatic compositions are non-inflammatory, and are degraded in an animal's body after successfully re-establishing hemostasis of a tissue site. Methods for utilizing such compositions are also provided.

All documents cited in this patent are incorporated herein by reference in their entireties.

Vascette™ VCD hemostatic applique' is a geometric (square, rectangular, oval, circular oo irregular shape), single use, multi-layer, topical, hydrophilic wound dressing applied over vascular puncture sites and percutaneous catheter sites (before or after formation of the puncture wound). Vascette™ VCD is, by way of non-limiting example, a square (50 mm×50 mm), multi-layer bandage that incorporates a topical hemostatic foam agent. Foam dimensions are 25 mm×25 mm×4 mm (thick). The underside of the bandage has a biocompatible adhesive coating with a protective, peel-away liner. The hemostatic foam is affixed to the center of the bandage and visible from the topside of the dressing. All materials employed in the device are biocompatible or low allergenic. The strippable cover layer need not be so limited. Upon application, there will be no compression applied to the bandage. The hemostatic foam will be positioned directly over the skin surface puncture site. The polysaccharide, ultra-hydrophilic foam rapidly absorbs water from blood, producing a hemoconcentration of solid blood components (platelets, red blood cells, fibrinogen, etc.), typically producing hemostasis within four to six minutes after application.

2. Modified Starch Processing and Mode of Action: Starches are modified to enhance their performance in different applications. Starches may be modified to increase their stability against excessive heat, acid, shear, time, cooling, or freezing; to change their texture; to decrease or increase their viscosity; to lengthen or shorten gelatinization time; or to increase their visco-stability. Pursuant to FDA guidance, following is a description of the polysaccharide chemistry and modified starch processing. AMP® particles or foam are plant derived modified starch (chemical name: carboxyl starch sodium; CMS), which is a granular polysaccharide polymer obtained by physical processes, including granulation and sieving. The particle size of AMP® is in the range of 10~300 μm. The sodium starch glycolate (CMS) contains no medicinal substance or human/animal derivatives. It is a cold water-soluble starch derivative having wide applications in the fields of pharmaceutical, textile, paper making, adhesive and absorbent. CMS is included in the United States Pharmacopoeia (USP NF36<5576>), Europe Pharmacopoeia (EP 5.4 p. 4018-4019) and Chinese Pharmacopoeia (Ch.P. 2020 Vol 4 P791) based hemostat particles have a broad range of applications and proven hemostatic effect. To date, there are no known product related adverse events. The foam configuration is preferably a lyophilized version of the AMP® particles contained in the Responder® topical hemostat (K191377 pending). The foam tradename is SealFoam™ foam cushion. The CMS Foam Molecular Structure is similar to that shown in FIG. 3.

The preferred polysaccharide components for the porous particles and porous beads of the present invention may often be made from cross-linked polysaccharides, such as cross-linked dextran (poly[beta-1,6-anhydroglucose]) or starch (poly{alpha-1,4-anhydroglucose]). Dextran is a high molecular weight water-soluble polysaccharide. It is not metabolized by humans, is non-toxic, and is well tolerated by tissue in most animals, including most humans. There has even been extensive use of solubilized dextrans as plasma substitutes. Similarly, beads prepared by cross linking starch with epichlorohydrin are useful as hemostatic agents and are well tolerated by tissue. The starch particles are enzymatically degraded by tissue alpha-amylases and rapidly removed from the wound site. The Sephadexm™ beads specifically mentioned in the description of particularly useful polysaccharides comprise dextran crosslinked with epichlorohydrin. These beads are available in a variety of bead sizes (e.g., 10 to 100 micrometers, with a range of pore size. It is believed that pore sizes on the order of from 5 to 75% of volume may be commercially available and can be expanded to from 5 to 85% by volume or manufactured with those properties from amongst the type of beads described above. The sizes of the pores may also be controlled to act as molecular sieves, the pore size being from 0.5% or 1 to 15% of the largest diameter of the particles or beads. The Sephadex™ beads are promoted as having controlled pore sizes for molecular weight cutoff of molecules during use as a sieve, e.g., with cutoff molecular being provided at different intervals between about 5,000 Daltons and 200,000 Daltons. For example, there are cutoff values specifically for molecular weight sizes of greater than 75,000 Daltons. This implies a particle size of specifically about 10 to 40 microns. These beads will rapidly absorb water, swelling to several times their original diameter and volume (e.g., from 5 to as much as twenty times their volume). Similar technology can be used to produce cross linked starch beads with properties similar to the Sephadex™ particles. Other soluble polysaccharides such as sodium alginate or chitosan can be used to prepare cross linked beads with controlled porosity and size.

Major classes of pressure-sensitive adhesives include tackified natural rubbers; synthetic rubbers such as butyl rubber; and tackified linear, radial, star, and branched and tapered styrene block copolymers, such as styrene-butadiene, styrene-ethylene/butylene and styrene-isoprene; polyurethanes; polyvinyl ethers; acrylics, especially those having long chain alkyl groups; poly-.alpha.-olefins; and silicones.

Generally, when additives are used to alter properties of pressure-sensitive adhesives, the additives need to be miscible with the pressure-sensitive adhesive or to form homogeneous blends at the molecular level. Some types of pressure-sensitive adhesives have been modified with tackified thermoplastic elastomers, thermoplastics, and elastomers. For example, thermoplastic materials have been added to polymerized hot melt acrylic pressure-sensitive adhesives wherein the thermoplastic is a packaging material or recyclable tape backings. In these cases, the type and amount of thermoplastic material is controlled so that the thermoplastic material can function as a packaging material while avoiding degradation of the adhesive properties of the pressure-sensitive adhesive.

However, more often than not when a non-tacky thermoplastic additive is blended with a pressure-sensitive adhesive, reduction of the overall adhesive properties of the blend (as compared to the pressure-sensitive adhesive only) are observed. Thermoplastic polymers have been added to styrene block copolymer adhesives to reduce the tack of the resulting pressure-sensitive adhesives for application of protective sheets to large area surfaces.

Pressure-sensitive adhesives, whether modified or not have been used for more than half a century for a variety of purposes. Generally, pressure-sensitive adhesives are used in tapes wherein a tape comprises a backing, or substrate, and a pressure-sensitive adhesive. Typically, a pressure-sensitive adhesive adheres with no more than applied finger pressure and can be permanently tacky.

In the medical field, pressure-sensitive adhesive tapes are used for many different applications in the hospital and health areas. For most applications, tapes are applied directly to a patient's skin. It is important that the pressure-sensitive adhesive tape be compliant and non-irritating to the skin, as well as adhering to the skin without causing damage to the skin when the tape or adhesive coated article is removed. A particularly useful medical application for pressure-sensitive adhesive tapes and articles is in the field of transdermal patches. Such patches can be used as drug transport membranes or to attach drug transport membranes to skin.

Although pressure-sensitive adhesive tapes and articles are widely used in the medical field, pressure-sensitive adhesive tapes and articles find widespread use in many other applications. For example, transfer tapes can be used to adhere two surfaces together such as the flaps of packing material or fabric to a surface. However, transfer tape adhesives generally have little tensile strength and one solution has been to add glass fibers to provide tensile strength.

Pressure-sensitive adhesives require a delicate balance of viscous and elastic properties that result in a four-fold balance of adhesion, cohesion, stretchiness and elasticity. Pressure-sensitive adhesives generally comprise elastomers that are either inherently tacky, or elastomers or thermoplastic elastomers that are tackified with the addition of tackifying resins.

FIG. 1 is an exploded side view of an embodiment of the therapeutic device 100 of the invention. Shown in the device 100 is a release layer 102 and an optional adhesive layer 106 (which will not block access to the hemostatic foam layer 108). Surrounding the hemostatic foam layer 108 is the structural foam layer 104. An adhesive layer 110 secures the hemostatic layer 108 and the structural foam layer 104 to a support layer 112 with an edge 114. The release layer 102 is removed and the structural foam layer 104 and the hemostatic foam layer 108 are pressed against the area (e.g., skin, not shown) to be addressed by treatment with the device 100.

Figure 2:
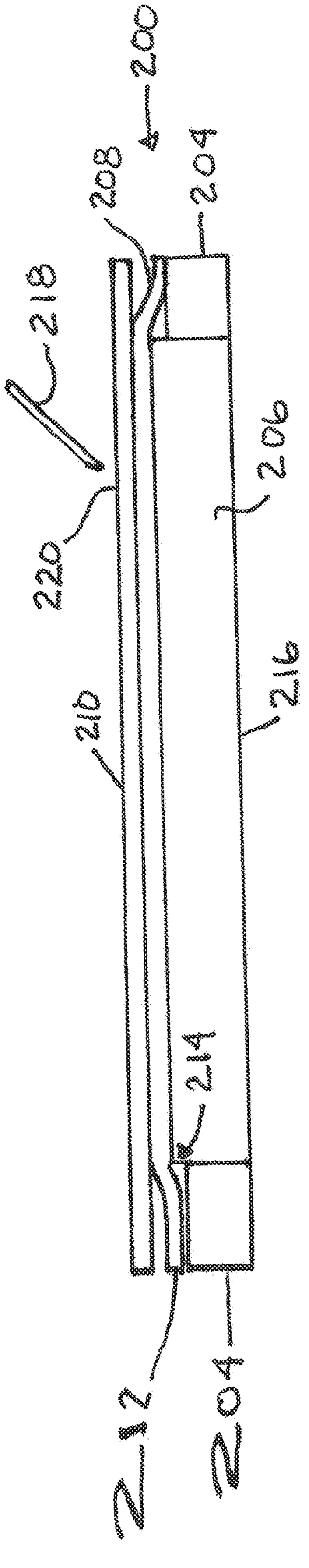
FIG. 2 is a side view of an embodiment of the therapeutic device of the present invention applied to the skin of a patient and with a needle penetrating through the device.

FIG. 2 is a side view of an embodiment of the therapeutic device 200 of the present invention (after removal of the strippable release layer 102 of FIG. 1) applied to the skin of a patient 202 and with a needle 218 penetrating through the device 200. The hemostatic foam layer 206 and the structural foam layer 204 are pressed against the skin 202 of the patient. The adhesive layer 208, 212 is shown as more of a structural layer, putting tension on the edges 214 of the hemostatic foam layer 206 to assure firm contact of the hemostatic layer 206 against the skin 202. The support layer 210 is now distal from the skin 202. A needle or catheter 218 is shown penetrating through the support layer 210 at a point 220. The needle or catheter 218 continues passing through the adhesive layer 208 and through the hemostatic foam layer 206 and into the skin 202 of the patient. The interface 216 between the hemostatic foam layer 206 and the skin 202 creates a hemostatically active line 216 where blood from the needle or catheter 218 penetrating the skin will clot.

Figure 2A:
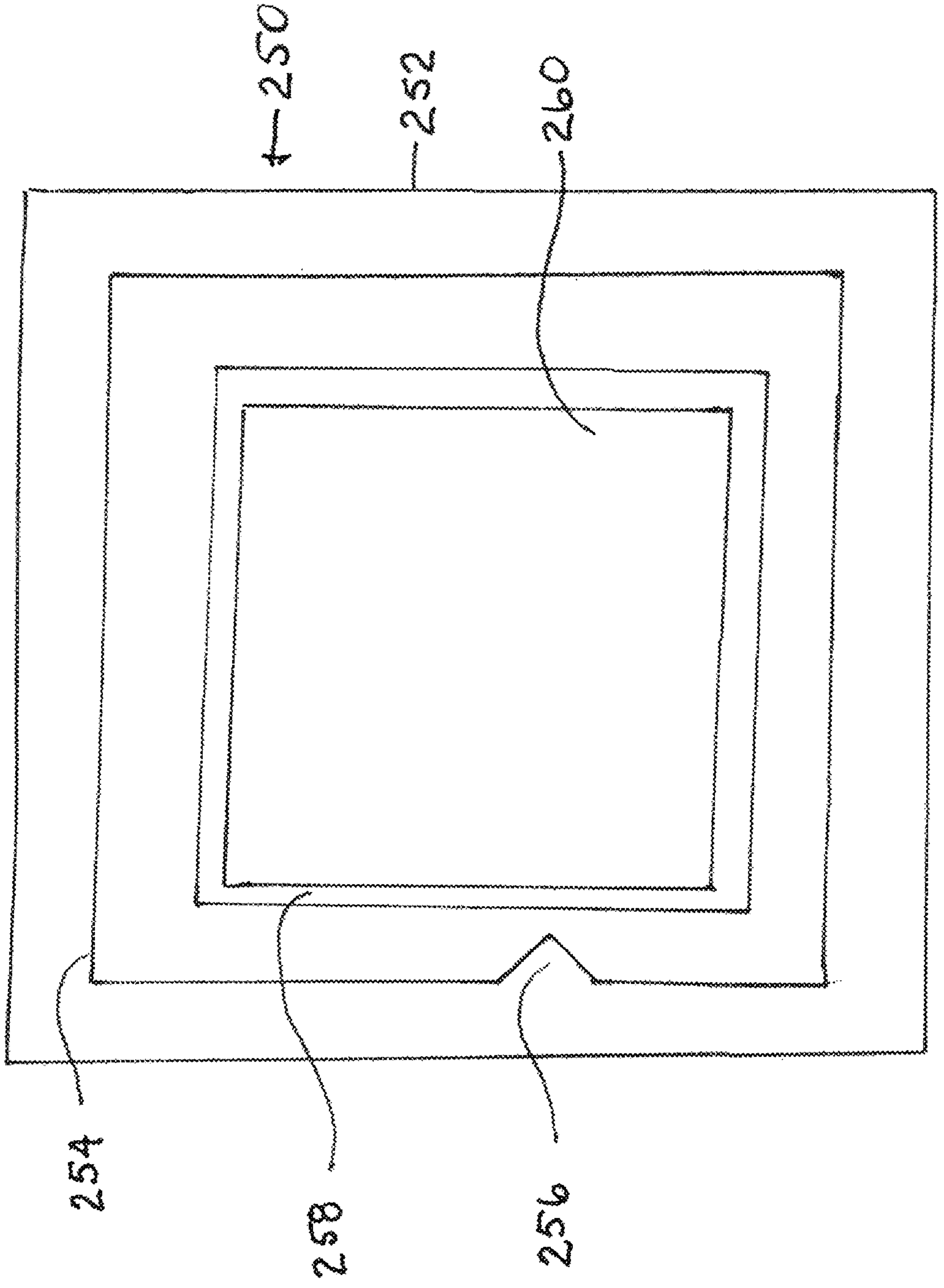
FIG. 2A is a vertical view of a device according to the scope of the present invention.

FIG. 2A is a vertical view of a device 250 according to the scope of the present invention. The support layer 252 is behind the structural support foam 258 and the hemostatic foam layer 260. The strippable release layer 254 is shown over both the structural foam layer 258 and the hemostatic foam layer 260. A notch 256 is shown to facilitate removal of the release layer 254.

Figure 2B:
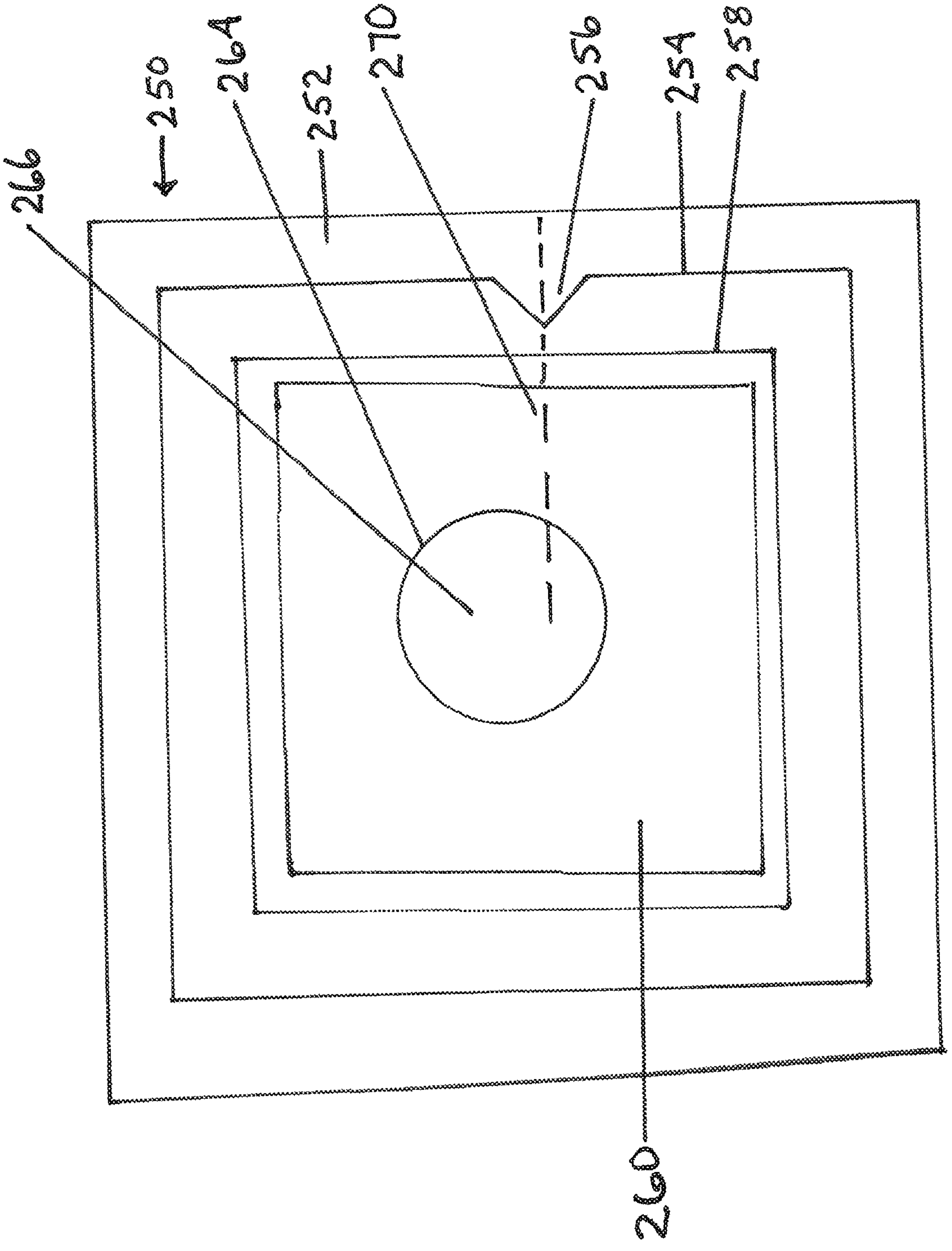
FIG. 2B is a vertical view of a device according to the scope of the present invention with the device of FIG. 2C shown with a slit along a line through the entire depth of the device to enable a liquid feed tube to the foam, through the device.
Figure 2C:
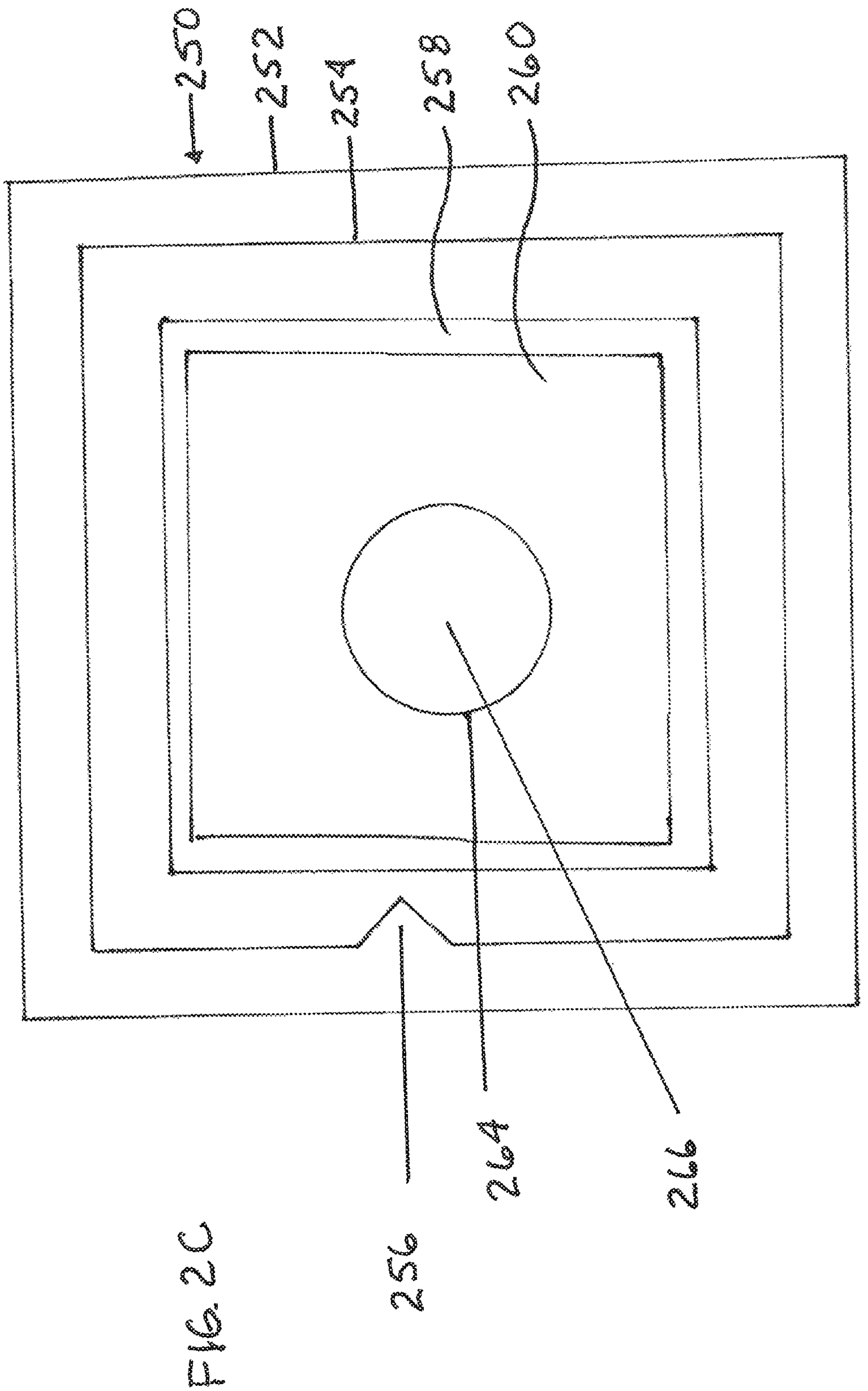
FIG. 2C is vertical view of a device according to the scope of the present invention, with an improved structure to facilitate direction of water through the device.

FIG. 2B is a vertical view of a device 250 according to the scope of the present invention with the device of FIG. 2C shown with a slit 270 along a line through the entire depth of the device to enable a liquid feed tube to the hemostatic foam layer 260, through the device.

FIG. 2C shows the vertical view of the device 250 of FIG. 2A used as a dressing with an improvement in the addition of an opening or hole 264 that provides a window in the hemostatic foam layer 260. Beneath the window lies a foam layer 258 acting as a pad which is preferably the hemostatic, polysaccharide starch described herein in the practice of the invention. When the hemostatic starch is applied to a bleeding arteriotomy it rapidly absorbs water, creating a gelatinous mass which has a robust hemostatic reaction and is vigorously adhesive. When removal of the dressing is required, it is desirable to irrigate with water via the large window directly above the adhesive hemostat. Generous irrigation neutralizes adhesivity, facilitating removal of the dressing without disturbing the clotted arteriotomy. The water passes into the opening or hole 264, around and into the hemostatic foam layer, softening the self- and cross-adhesions of the hemostatic foam to the wound, and facilitating the removal of the applied dressing with reduced damage to a clot and reduced tension and damage to adjacent tissue.

If a wrap or cover is present over the applied dressing, it is of course removed before water is applied through the hole 264. The surface area of the hole 264 should be sufficient to allow situationally desirable rapid access for the water to the adhesive starch, typically within 1-45 seconds in sufficient amount to enable release of the dressing by reducing the degree of adhesiveness of the adhesive starch. The surface area of the hole 264 with respect to the surface area of the hemostatic foam layer 260 should be large enough to expose at least 5%, or at least 10%, and preferably between 15% and 85% in square centimeters and preferably between 25% and 75% of the backside of the hemostatic foam layer 260. The relative dimensions are a balance between the need for enabling speed of release and protecting the hemostatic foam layer 260 from early release from ambient moisture. The hole 264 also allows any excess moisture to be wiped off the top of the dressing.

All numbers in FIGS. 2A, 2B, 2C and 2D that are common to each other are identical elements as among the Figures.

Figure 2D:
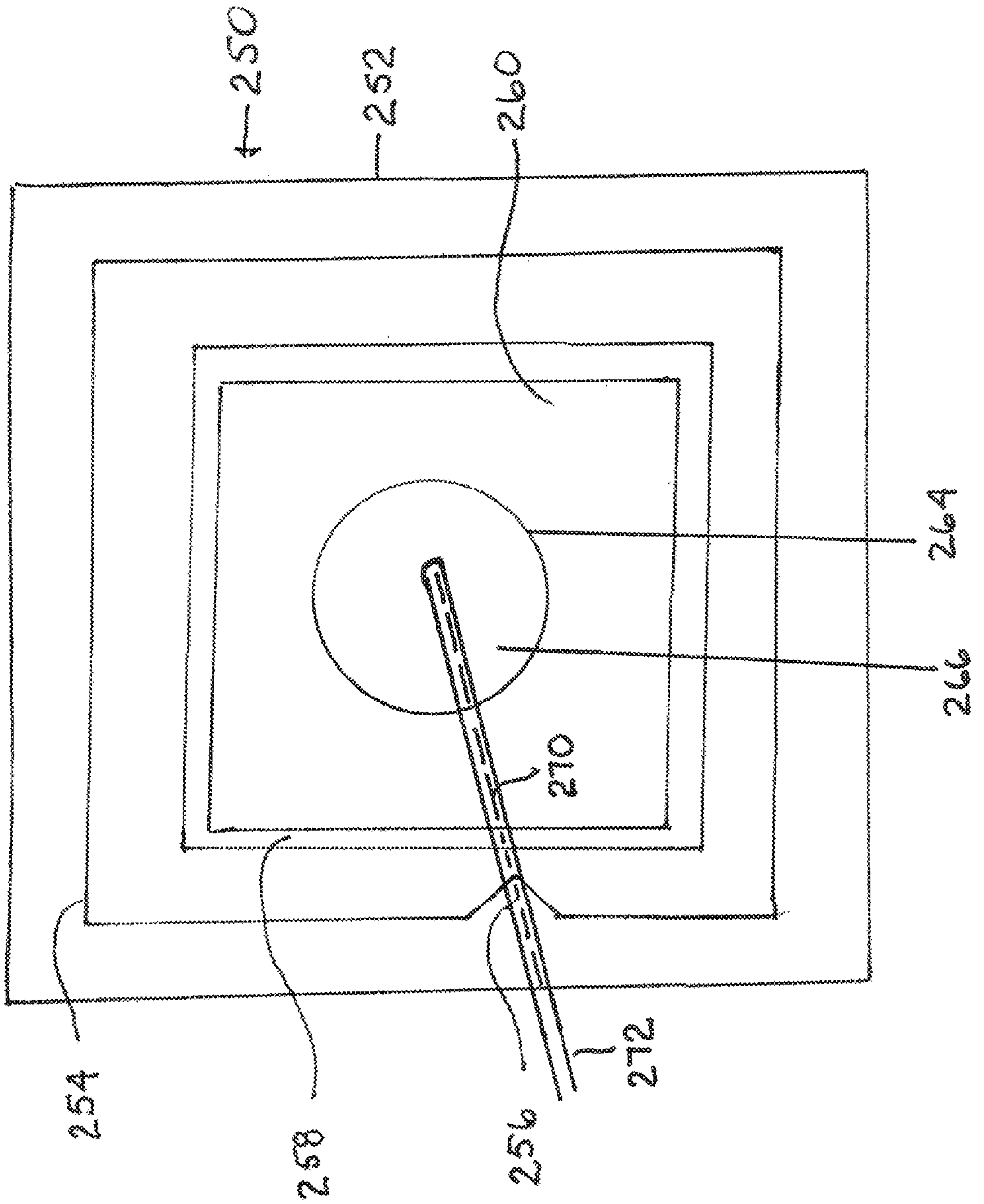
FIG. 2D is a vertical view of a device according to the scope of the present invention with the device of FIG. 2C shown with a feeding tube inserted through the slit of FIG. 2B along a line through the entire depth of the device to enable a liquid feed tube to the foam, through the device.

FIG. 2D is a vertical view of a device 250 according to the scope of the present invention with the device of FIG. 2B shown with a feeding tube 272 inserted into and through the slit 270 of FIG. 2B along a line through the entire depth of the device to enable a liquid feed tube to the foam, through the device. The slit 270 may be pulled open to allow the feeding tube 272 to be secured within the pathway created by the slit 270. Tension within the slit 270 will assist in holding the feed tube 272 stable while fluids are introduced (or even withdrawn) from the wound site. The slit 270 and the feed tube 272 typically are aligned within the edges of the notch 256 to facilitate alignment and stability of the feeding tube 272.

FIG. 3 is a non-limiting rendition of chemical structure for a hemostatic foam useful un the practice of the present invention.

Other variations in the compositions and dimensions and structure of the device can be practiced without deviating from the scope of the invention set forth in the claims.

These and other aspects of the invention will be further understood by reference to the figures.

What is claimed:

1. A hemostatic surface application device having a region of hemostatic foam for contact with a patient's skin where a wound exists or is created, the device comprising: a) a release layer, b) the release layer in contact with a hemostatic flexible foam layer, c) a structural foam layer having a front side and a back side surrounding the hemostatic flexible foam layer, forming a generally central hemostatic surface exposed through the front side of the surrounding structural foam layer, and d) a support layer adhered to the back side of the structural foam layer, the support layer has an opening therein which exposes at least 5% of the back side of the structural foam layer to enable water to irrigate the hemostatic foam layer during removal of the device from contact with the patient's skin, and wherein there is a slit through a), b) and c) which allows insertion of a liquid feeder tube enabling liquid flow to and from the hemostatic flexible foam layer.

2. The device of claim 1 wherein the hemostatic flexible foam layer retains at least 99.5% of total weight of the hemostatic flexible foam layer when in contact with a surface having a 5 micron thick layer of water on its surface for 1 minute, wherein the hemostatic flexible foam layer extends over the surrounding structural foam layer, and further wherein an opening in the structural foam layer exposes at least 5% of the back side of the hemostatic flexible foam layer to enable water to irrigate the hemostatic flexible foam layer during removal of the device from contact with the patient's skin.

3. The device of claim 2 wherein the hemostatic flexible foam layer comprises a polysaccharide foam composition.

4. The device of claim 2 wherein the structural foam layer is a polyurethane foam.

5. The device of claim 1 wherein the hemostatic flexible foam layer comprises a polysaccharide foam composition.

6. The device of claim 1 wherein the hemostatic flexible foam layer has a thickness at least 1% greater than a thickness of the structural foam layer.

7. The device of claim 6 wherein the structural foam layer is a polyurethane foam.

8. The device of claim 6 wherein the opening in the support layer exposes at least 10% of total surface area of the hemostatic flexible foam layer.

9. The device of claim 8 wherein the opening in the support layer exposes 15-85% of total surface area of the hemostatic flexible foam layer.

10. The device of claim 9 wherein the support layer is adhered to the back side of the structural foam layer by an adhesive layer.

11. A method of reducing excessive blood flow off an exterior surface wound of a patient comprising removing the release layer off the hemostatic surface application device of claim 1, applying the hemostatic surface to a limited area of skin of the patient, an extension of the hemostatic flexible foam layer assuring firm contact of the hemostatic flexible foam layer against the patient's skin, allowing clotting to occur on the exterior surface of the wound, applying an aqueous solution to the opening to soften the hemostatic flexible foam layer, and removing the device from the wound of the patient, and liquid is fed to the hemostatic layer through a liquid feeder tube.

12. A method of reducing excessive blood flow off an exterior surface wound of a patient comprising removing a release layer of a hemostatic surface application device comprising a region of hemostatic flexible foam for contact with the patient's skin where a wound exists or is created, the device comprising: a) a release layer, b) the release layer in contact with a hemostatic flexible foam layer, and c) a structural foam layer having a front side and a back side surrounding the hemostatic flexible foam layer, forming a hemostatic surface exposed through the front side of the surrounding structural foam layer, and d) a support layer adhered to the back side of the structural foam layer, wherein the support layer has an opening therein which exposes at least 5% of the back side of the hemostatic flexible foam layer to enable water to irrigate the hemostatic flexible foam layer during removal of the device from contact with the patient's skin and applying the hemostatic surface to a limited area of skin of the patient, wherein there is a slit through a), b), c) and d) which allows insertion of a liquid-feeder tube enabling liquid flow to and from the hemostatic flexible foam layer, and the slit is opened and the liquid-feeder tube accessing the hemostatic foam layer is fed into the slit.

13. The method of claim 12 wherein after applying a generally central hemostatic surface to the limited area of skin of the patient, and after clotting has initiated, applying an aqueous solution to the opening through the liquid-feeder tube, allowing water in the aqueous solution to soften the generally central hemostatic surface to facilitate removal of the device.

14. The method of claim 13 wherein the opening in the support layer exposes at least 10% of total surface area of the hemostatic flexible foam layer.

15. The method of claim 14 wherein the hemostatic flexible foam layer retains at least 99.5% of total weight of the hemostatic flexible foam layer when in contact with blood exuding from the skin of the patient for 1 minute.

16. The method of claim 15 wherein the hemostatic flexible foam layer comprises a polysaccharide foam composition.

17. The method of claim 15 wherein the hemostatic flexible foam layer has a thickness at least 1% greater than a thickness of the structural foam layer.

18. The method of claim 12 wherein the opening in the support layer exposes 15-85% of total surface area of the hemostatic flexible foam layer and a water solution is applied to the opening through the liquid-feeder tube.

19. The method of claim 11 wherein the hemostatic flexible foam layer comprises a polysaccharide foam composition.

20. The method of claim 19 wherein the hemostatic flexible foam layer has a hole through it allowing direct moisture contact to the hemostatic flexible foam layer and moisture is applied through the opening by the liquid-feeder tube, reducing adhesiveness of the hemostatic flexible foam layer prior to removing the hemostatic surface of the application device from the skin of the patient.

* * * * *